United States Patent [19]

Mori

[11] Patent Number: 4,984,862
[45] Date of Patent: Jan. 15, 1991

[54] LIGHT RADIATOR FOR THE CULTIVATION OF FISH

[76] Inventor: Kei Mori, 3-16-3-501, Kaminoge, Setagya-ku, Tokyo, Japan

[21] Appl. No.: 445,236

[22] Filed: Dec. 4, 1989

[30] Foreign Application Priority Data

Jan. 9, 1989 [JP] Japan .................................... 1-2238
Jul. 28, 1989 [JP] Japan .................................... 1-196060

[51] Int. Cl.$^5$ .......................... G02B 6/00; G02B 6/14
[52] U.S. Cl. .................................................. 350/96.10
[58] Field of Search ................ 350/96.10, 96.15, 96.29

[56] References Cited

U.S. PATENT DOCUMENTS 4,815,815  3/1989  Mori ................................. 350/96.10
4,822,123  4/1989  Mori ................................. 350/96.10

Primary Examiner—William L. Sikes
Assistant Examiner—Robert E. Wise
Attorney, Agent, or Firm—Jordan and Hamburg

[57] ABSTRACT

A light radiator for use in the cultivation of fish is described. The device includes a light guide for introducing light rays therein through its end portion and emits the same through its peripheral surface, a first-transparent container for hermetically accommodating therein the light guide and a second semitransparent container for hermetically accommodating therein the first transparent container. The second container is placed in water so as to outwardly project the light through the semi-transparent container.

10 Claims, 5 Drawing Sheets

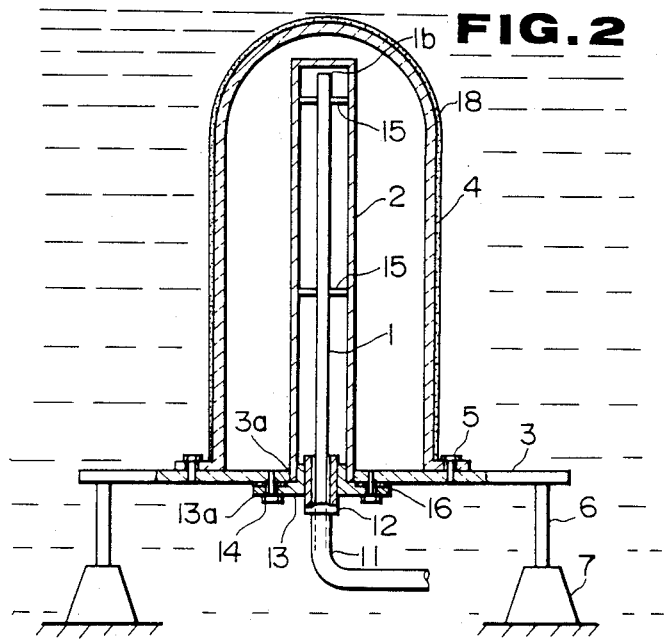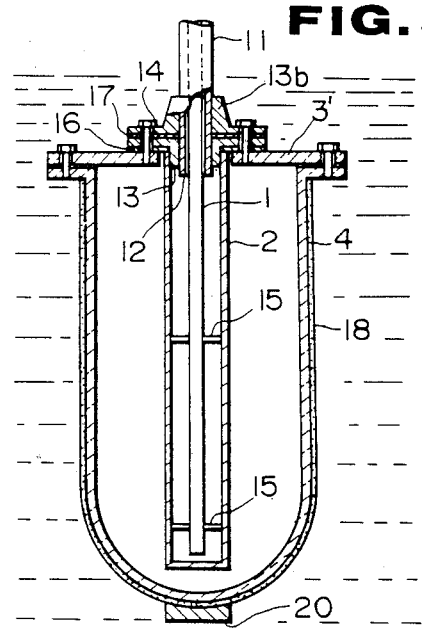

4,984,862

LIGHT RADIATOR FOR THE CULTIVATION OF FISH

BACKGROUND OF THE INVENTION

The present invention relates to a light radiator to be used in the cultivation of fish capable of receiving light energy transmitted through a fiber optic cable and for effectively radiating the same into water in order to produce algae and like plants for feeding and thereby raising fish.

In recent years, in relation to the necessity for saving energy, the effective utilization of solar energy has been actively studied and developed in various fields. The most effective utilization of solar energy is realized when it is used as light energy without being converted into thermal energy or electrical energy. From this point of view the present applicant has proposed various methods and systems for introducing solar rays focused by means of a lens system or the like into a fiber optic cable and to transmit the same therethrough to wherever the light is needed for illumination.

In any fish farm there is a great demand for zooplankton which eats algae to propagate itself. To effectively grow the algae it is necessary to properly supply the algae with sunlight and carbon dioxide. Generally, when algae increases and densely gathers, it may obstruct the light thereby preventing further propagation of the zooplankton.

The present applicant previously proposed a light radiator which is suitable for use in a chlorella culturing plant. An input end of the fiber optic cable is connected to a solar ray collecting device previously proposed by the present applicant, the device being intended to focus solar rays through a lens or the like and for introducing the focused solar rays into a fiber optic cable through which said solar rays are transmitted to wherever the light is needed. The solar rays collected by the above-mentioned solar ray collecting device are delivered through the fiber optic cable to a light-radiating device.

A light groove is spirally cut on the surface of the light guide's body. The light rays transmitted through the optic cable are introduced into the light guide and the light rays introduced into the light guide are reflected on the grooved portion and effectively radiated therefrom. In this case a substantially uniform radiation of the light from the whole body of the light guide may be achieved if the spiral groove is made in such a way that the spiral pitch gradually becomes narrow in the direction of the light being guided. Furthermore, when a reflecting plate or the like is placed at the end face of the light guide, the light reflected by the reflecting plate enters back into the light guide and is radiated therefrom. Furthermore, the light guide may be used hermetically enclosed in a semi-transparent or a transparent container to protect the light guide from being damaged by any other object. When the light guide, thus protected in the container, is used in water as a light source, its surface can always be prevented from a kind of fur forming on its surface and the radiation can be spread out more uniformly through the transparent container.

Another light-radiating device previously proposed by the present applicant has a light diffuser and a transparent or semi-transparent container.

The transparent or semi-transparent closed container is placed in water and the light rays transmitted through the fiber optic cable are diffused by the light diffuser and the diffused light rays are radiated into the water through the transparent or semi-transparent wall of the closed container. Consequently, algae may grow on the outer surface of the closed container and fish will gather around the closed container being attracted by the radiated light they and will eat the algae on the container's surface. The above-mentioned underwater light-radiating device is to be placed in water for cultivating aquatic plants and animals but when it is submerged deeply and, if its closed container is made of a plastic material that has thin walls, said container may be crushed by the increased water pressure thereby defeating the intended purpose.

SUMMARY OF THE INVENTION

It is an object of the present invention to provide a light radiator suitable for use in water as a light source for growing algae which can feed and cultivate fish.

It is another object of the present invention to provide an underwater light-radiating device which can be used in deep water without being crushed by the increased water pressure.

BRIEF DESCRIPTION OF THE DRAWINGS

FIGS. 2 and 3 illustrate respectively light radiators embodying the present invention;

DESCRIPTION OF THE PREFERRED EMBODIMENTS

Figure 1:
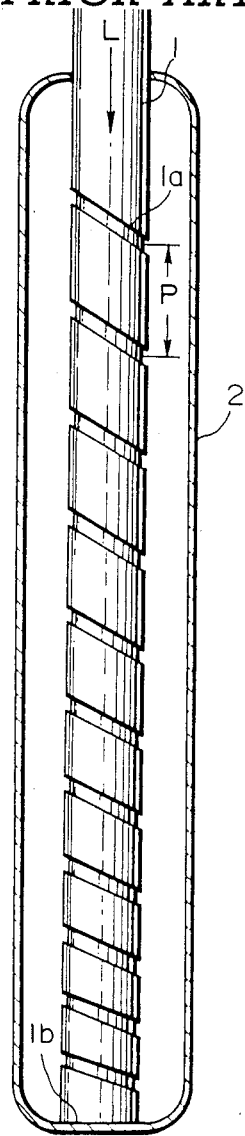
FIG. 1 is a view for explaining an embodiment of a light radiator previously proposed by the present applicant.

FIG. 1 is an enlarged sectional side view for explaining a light radiator previously proposed by the present applicant which is suitable for use in a chlorella culturing plant. In FIG. 1, 1 is a light guide and 1a is a groove spirally cut on the surface of a light guide's body. The light L introduced into the light guide 1 is reflected on a grooved portion 1a thereof and effectively radiated therefrom. In this case a substantially uniform radiation of the light L from the whole body of the light guide may be achieved, if the spiral groove 1a is made in such a way that the spiral pitch P gradually becomes narrow in the direction of guiding the light L. Furthermore, when a reflecting plate 1b or the like is placed at the end face of the light guide, the light reflected by the reflecting plate enters back into the light guide 1 and then is radiated radially therefrom. As shown in FIG. 1, the light guide may be used as hermetically enclosed in a semi-transparent or a transparent container 2 to protect the light guide from being damaged by any other object. Furthermore, when the light guide, thus protected in the container, is used in water as a light source, its surface can always be prevented from developing kind of fur on its surface and consequently its radiation can be spread out more uniformly through the transparent container.

In view of the foregoing, it is possible to provide a light radiator suitable for use in water as a light source for growing algae which can feed and cultivate fish.

FIG. 2 shows a light radiator embodying the present invention. In FIG. 2, numeral 1 designates a light guide having the same or analogous functions to the light guide referred to in FIG. 1. Said light guide 1 has one end as is or with a reflecting plate 1b bonded thereto and has the other end tightly or adhesively connected by means of a connector 12 to the end of a fiber optic cable 11 which is connected at the other end to a light source so as to transmit therethrough light energy from the light source. Light rays introduced into the fiber optic cable through its light-receiving end, not shown in FIG. 2, need to have wavelengths suitable to grow algae and also which are attractive to small fish. According to their reactions to the illumination, fish can be divided roughly into three groups i.e. fish willing to approach; fish that are frightened away and fish having no reaction to the light. Generally speaking, fish have a tendency to dislike and therefore scatter away from blue light rays and to be indifferent to or even willing to approach red light rays. In practical experiments, most fish were confused and scattered away when the illumination was with a blue colored light from an argon laser while many fish swam away when illuminated with a xenon lamp containing a large amount of ultraviolet rays. On the contrary, many fish approached green colored light. When radiation was made with a red colored light beam from a helium laser, some fish approached the beam but others showed no reaction. As is apparent from the above-mentioned facts, since the light passed through the algae being cultured assumes a green color, it may be suitable for cultivating fish. A transparent cylindrical container 2, in which the light guide 1 is accommodated and held at the center thereof by means of holding rings 15, is firmly secured to a fixture 13 in which the connector 12 of the light guide is fitted water-tight. The fixture 13 is secured water-tight at its flange 13a to a base plate 3 by means of bolts 14 and a packing 16 in such a way that the transparent cylindrical container 2 and the light guide 1 pass through a hole 3a of the base plate 3. A semi-transparent cylindrical container 4 is secured to the base plate 3 so as to enclose therein the transparent container 2 ensuring concentricity with the light guide 1. The base plate 3 has supporting legs which bear the peripheral portion of the base plate against the light guide 1 and each of which is provided with an anchor 7 so as to be stably installed on the bottom of the water at the time of underwater light radiation from the light guide 1. As mentioned above, the light radiator according to the present invention is constructed in such a way that the light guide 1 is hermetically enclosed in the transparent container 2 which in turn is hermetically enclosed in the semi-transparent container 4, and said container 4 is used in an evacuated state (however, if water enters into the container 4 at the time of placing the radiator in water, air may be blown into the container 4 from the lower side through an air hose) so as to soften the light to be emitted through its semi-transparent wall and thereby to easily produce algae 18 around its outer surface. Consequently, the outer surface of the semi-transparent container 4 becomes suitable for propagating algae 18 and may be covered with the algae 18 through which green colored light is emitted into water and fish, being attracted by said green-colored light, may approach the radiator and eat the algae 18 adhering to the outer surface of the semi-transparent container 4. Since the algae 18 grown at the outer surface of the semi-transparent container 4 are eaten by fish, it is best to supply the correct amount of light as is needed in order to realize the desired effect. In other words, thanks to such good circulation, the algae grows and fish eat them. The radiator can constantly emit enough light to attract fish to it and is therefore effective at gathering fish.

FIG. 3 shows another embodiment of the present invention. Unlike the above-mentioned light radiator installed on the water bottom as shown in FIG. 2, this is a light radiator which is provided with a weight 20 so as to be hung in water. The main components of the radiator are the same as that shown in FIG. 2. In FIG. 3, parts having the same functions as those of like parts shown in FIG. 2 are denoted by the same numbers and a detailed explanation will be omitted. A light guide 1, a transparent cylindrical container 2 and a semi-transparent container are concentrically installed on a round-shaped base plate 3' and secured thereto in the same manner as described for the light radiator shown in FIG. 2. However, in FIG. 3, a fiber optic cable 11 is used as a hunger cable of the radiator and is provided with a mounting flange 13b which is screwed on a connecting part 12 and threadably secured by bolts 14 to the base plate 3' in such a way as to press puckings 16, 17 between the base plate 3' and the mounting flange 13b. The light radiator thus assembled into one unit can be hung in water by the fiber optic cable 11 and be used for culturing algae used for feeding fish in the same way as the light radiator shown in FIG. 2 does. The light radiator shown in FIG. 3 is suitable for use in deep water. The light radiated from this light radiator through the semi-transparent container is so soft that algae may be effectively grown and fish are willing to approach the radiator.

As is apparent from the foregoing description, according to the present invention, it may be possible to provide a light radiator which, having a double sealed construction composed of a transparent container 2 hermetically enclosing therein a light guide 1 and a semi-transparent container 4 hermetically enclosing therein said transparent container 4, can project light rays through the semi-transparent container 4 having a large diameter, namely, a large external surface enough to grow large amounts of algae for feeding small fish. Furthermore, since algae passes green-colored light through themselves, small fish are willing to gather around the source of radiation and eat the algae adhering to the outer surface of the light radiator. This eliminates the possibility of obstructing the light radiation by excessive propagation of the algae on the outer surface of the light radiator and makes it possible to always and effectively feed small fish. Light radiated from the light radiator through the semi-transparent container 4 is so soft that algae are easily produced and fish are not frightened away.

Figure 4:
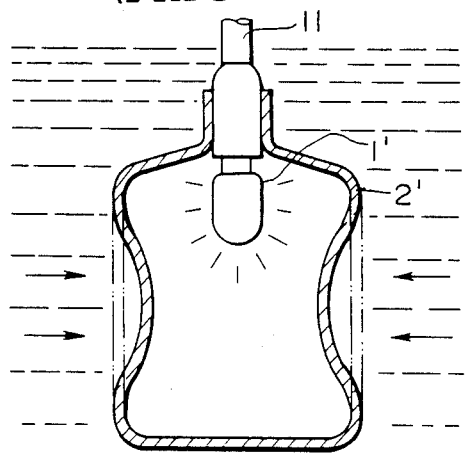
FIG. 4 is a view for explaining another example of a light-radiating device which can be used in deep water previously proposed by the present applicant.

FIG. 4 is a view for explaining an underwater light-radiating device previously proposed by the present applicant. In FIG. 4, 11 is a fiber optic cable, 1' is a light diffuser and 2' is a transparent or semi-transparent container. An input end, not shown, of the fiber optic cable 11 is connected to a solar ray collecting device previously proposed by the present applicant (said device being intended to focus solar rays through a lens or the like and for introducing the focused solar rays into a fiber optic cable through which said solar rays are transmitted to wherever the light is needed.) The solar rays collected by the above-mentioned solar ray collecting device are delivered through the fiber optic cable 11 to an underwater light-radiating device. The transparent or semi-transparent closed container 2' is placed in water and the light rays transmitted through the fiber optic cable 11 are diffused by the light diffuser 1' and then the diffused light rays are radiated into the water through the transparent or semi-transparent wall of said closed container 2'. Consequently, algae may grow on the outer surface of the closed container 2' and fish will gather around said closed container, being attracted by the radiated light, and eat the algae on the container's surface. The above-mentioned underwater light-radiating device is to be placed in water for cultivating aquatic plants and animals but when it is submerged deeply and, if its closed container 2' is made of a plastic material that has thin walls, said container 2' may be crushed by the increased water pressure thereby defeating the intended purpose.

In view of the foregoing, it is desirable to provide an underwater light-radiating device which can be used in deep water without being crushed by the increased water pressure.

Figure 5:
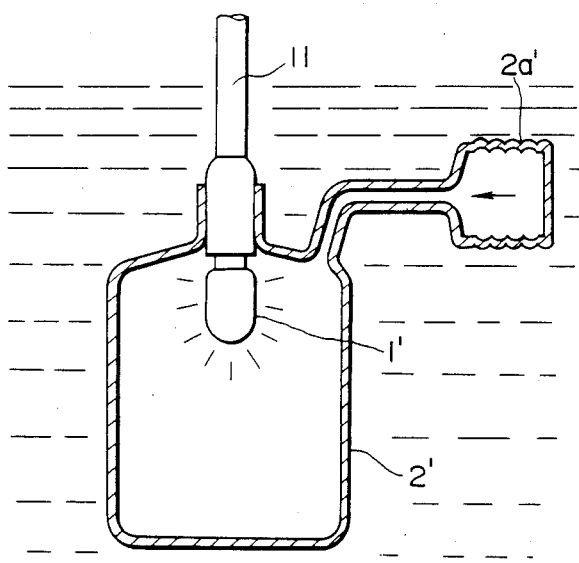
FIG. 5 is a view for explaining an underwater light-radiating device embodying the present invention.

FIG. 5 is a construction view for explaining an underwater light-radiating device embodying the present invention. In FIG. 5, elements which are similar in function to the elements of the prior art shown in FIG. 4 are given like reference numbers. According to the present invention, the device has a first closed container 2' and a second closed container 2a' which communicates with said first closed container 2' and is more flexible than the first one 2'. Consequently, when the light radiation device is placed in deep water, the second container 2a' may contract first because of the increased water pressure and transfer the air inside it to the first closed container 2' which by virtue of the increased air pressure can withstand the external water pressure outside it without contracting.

As is apparent from the foregoing description, according to the present invention, it may be possible to provide an underwater light-radiating device which, being provided with comparatively flexible transparent or semitransparent closed containers, can effectively be used in deep water without being crushed by the external water pressure.

Figure 6:
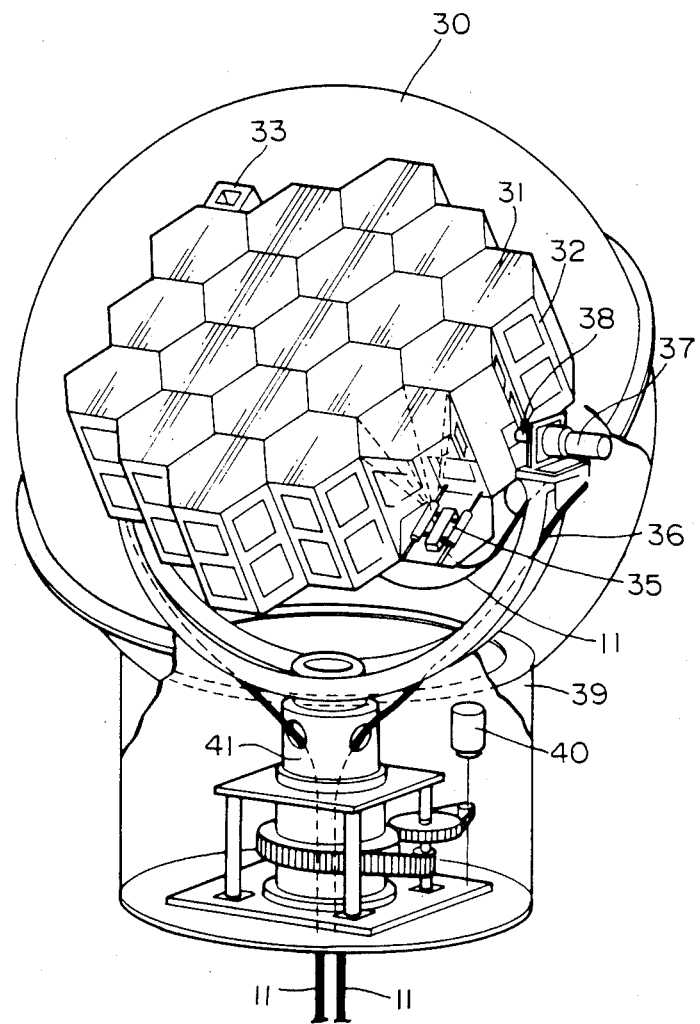
FIG. 6 is a view for explaining an embodiment of a solar ray collecting device proposed by the present applicant.

FIG. 6 is a construction view illustrating, by way of example, a solar ray collecting device previously proposed by the present applicant. In FIG. 6, numeral 30 is a transparent protective capsule, 31 is a Fresnel lens, 32 is a lens holder, 11 is a fiber optic cable consisting of a number of optical fibers located on the focal plane of the Fresnel lens, 35 is an optic cable holder, 36 is an arm, 37 is a pulse motor, 38 is a horizontal shaft to be rotated by said pulse motor 37, 39 is a base for mounting the protective capsule 30 thereon, 40 is a pulse motor, 41 is a vertical shaft to be rotated by the pulse motor 40.

The direction of the sun is detected by means of the solar position sensor 33 and its detection signal which controls the pulse motors 37 and 40 for rotating the horizontal shaft 38 and 41 respectively so as to always direct said solar position sensor 33 toward the sun, and the sunlight focused by each lens 31 is guided into the fiber optic cable 11 through its end surface set at the focal point of said lens. The optic cable 11 with their end faces placed at the corresponding lens focal planes, are bundled together and led out from the solar ray collecting device and laid any place where the light is needed for illumination, cultivation of plans, nurturing animals or fish, for sunbathing etc.

Figure 7:
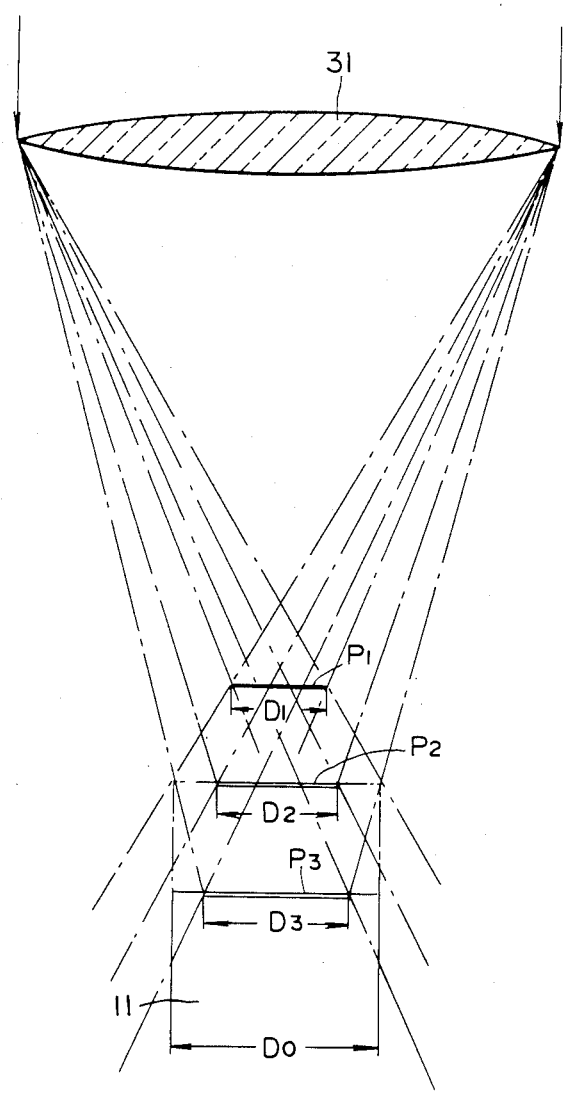
FIG. 7 is a view for explaining the principle for guiding the sunlight into a fiber optic cable.

FIG. 7 is a view for explaining how to guide the light rays collected by the lens 31 into the optic cable 11.

In FIG. 7, 31 is a Fresnel lens or the like and 11 is an optic cable for receiving the sunlight focused by said lens and for transmitting the same there-through to any desired place. In the case of focusing the sunlight through the lens system, the solar image has a central portion consisting of almost white light and a circumferential portion containing therein a large amount of the light components having wave-lengths corresponding to the focal point of the lens system. Namely, in the case of focusing sunlight through the lens system, the focal point and the size of the solar image will vary in accordance with the component wave-lengths of the light. For instance, the blue color light having a short wave-length makes a solar image of diameter D1 at position P1. Furthermore, the green color light makes a solar image of diameter D2 at position P2 and the red color light makes a solar image of diameter D3 at position P3.

Consequently, as shown in FIG. 7, when the light-receiving end-surface of the optical cable is set at position P1, it is possible to collect sunlight containing plenty of blue color components at the circumferential portion thereof. When the light-receiving end-surface of the optic cable is set at position P2, it is possible to collect sunlight containing plenty of green color components at the circumferential portion thereof. When the light-receiving end-surface of the optic cable is set at position P3 it is possible to collect sunlight containing plenty of red color components at the circumferential portion thereof. In each case, the diameter of the optic cable can be selected in accordance with the light components to be collected. For instance, the required diameters of the optic cable are D1, D2 and D3, respectively, depending on the colors of the light rays desired, i.e. the blue, green and red colors. In such a way, only the required amount of the fiber optic cable can be used and thereby the sunlight containing therein plenty of the desired color components can be collected most effectively.

And further, as shown in FIG. 7 if the diameter of the light-receiving end-surface of the optic cable is enlarged to D0, it may be possible to collect light containing therein all of the wavelength components.

It is also possible that the light-receiving surfaces of the optic cable 11 are fixed at the focal plane of the lens system beforehand by a manufacturer or said light-receiving surfaces of the optic cable are adjustable in the axial direction of the lens system and regulated by the user to a desired point so as to obtain the desired colored light.

As mentioned above, when the sunlight is focused through a lens system, the solar image has a central portion and a circumferential portion the content of which varies depending upon the distance from the lens system. Namely, at a short distance from the lens system blue color light is gathered and at a larger distance from the lens system red color light is gathered. By adjusting the set position of the light-receiving faces of the optic cable it is possible to eliminate infrared and ultraviolet rays from the sunlight and thus obtain sunlight that is suitable for sunbathing and for cultivating animals and plants.

The above-mentioned solar ray collecting device can be installed on a roof and the sunlight, collected by said device, transmitted through a fiber optic cable into a light radiator wherein the light is radiated for the purpose of nurturing fish as mentioned previously.

I claim:

1. A light radiator device which is useable underwater for cultivating fish, comprising a light guide having an end portion through which light rays are introduced and having a peripheral surface through which light rays are emitted, a transparent first container for hermetically accommodating said light guide such that light rays emitted from said light guide pass through said first container, and a semi-transparent second container for hermetically accommodating said first container such that light rays emitted from said light guide and passing through said first container pass through said second container into the surrounding water in which said light radiator is disposed.

2. A light radiator device according to claim 1, wherein said first container and said light guide each having a common longitudinal axis, said first container having an inner cylindrical wall, and holding rings disposed between said light guide and said inner cylindrical wall for holding said light guide in said first container in a position in which said peripheral surface of said light guide is spaced from said inner cylindrical wall of said first container.

3. A light radiator device according to claim 1, wherein said second container has a cylindrical part and a base plate, fastening means fastening said cylindrical part to said base plate, said base plate having an opening through which said first container extends, said first container having a longitudinal end, and mounting means mounting said longitudinal end of said first container on said base plate.

4. A light radiator device according to claim 3, where said mounting means comprises a fixture having a cylindrical portion and a flange, said cylindrical portion extending into said longitudinal end of said first container, said cylindrical portion having a passage through which said light guide extends, and fastening means fastening said flange portion to said base plate.

5. A light radiator device according to claim 1, wherein said first container has an outer cylindrical wall and said second container has an inner cylindrical wall spaced from said outer cylindrical wall of said first cylinder.

6. A light radiator device according to claim 1, wherein said light guide has a terminating end disposed in said first container and a reflecting plate bonded to said terminating end.

7. A light radiator device according to claim 1, wherein said second container has a cylindrical part and two longitudinal end parts, said cylindrical part having a longitudinal axis, one of said end parts being a generally flat base plate extending generally perpendicular to said longitudinal axis, the other of said end parts having the configuration of a hemisphere, said second container further comprising fastening means fastening said base plate to said cylindrical part.

8. A light radiator device according to claim 7, wherein said base plate has means for affixing said device to a fixed underwater position.

9. A light radiator device according to claim 1, wherein said second cylinder is floatable in the water in which the device is used for cultivating fish.

10. An underwater light-radiating device which is useable underwater for cultivating fish comprising a transparent first container, a light guide means extending into said first container and operable to emit light rays through said first container into the surrounding water, a second container, conduit means extending between said first and said second containers, said second container being more flexible than said first container such that when said device is used underwater and subjected to increasing underwater pressure, said second container will at least partially collapse before said first container due to said underwater pressure to thereby compress the air in said second container, thereby increasing the air pressure in said first container via said conduit means to prevent said first container from collapsing.

* * * * *